United States Patent
Kang et al.

(10) Patent No.: US 9,480,781 B2
(45) Date of Patent: Nov. 1, 2016

(54) ARTIFICIAL INTELLIGENCE PORTABLE SUCTION DEVICE HAVING A CATHETER REEL

(71) Applicant: LMECA CO., LTD., Wonju-si, Gangwon-do (KR)

(72) Inventors: Jung-kil Kang, Goyang-si (KR); Jin Jung, Seoul (KR); Jin-ho Roh, Gunpo-si (KR)

(73) Assignee: LMCA CO., LTD. (KR)

( * ) Notice: Subject to any disclaimer, the term of this patent is extended or adjusted under 35 U.S.C. 154(b) by 24 days.

(21) Appl. No.: 14/630,626

(22) Filed: Feb. 24, 2015

(65) Prior Publication Data

US 2015/0246165 A1    Sep. 3, 2015

(30) Foreign Application Priority Data

Feb. 28, 2014    (KR) .................. 10-2014-0023985

(51) Int. Cl.
| | | |
|---|---|---|
| A61M 15/00 | (2006.01) | |
| A62B 7/00 | (2006.01) | |
| A61M 1/00 | (2006.01) | |
| A61M 16/04 | (2006.01) | |
| A61M 25/01 | (2006.01) | |
| A61M 25/00 | (2006.01) | |

(52) U.S. Cl.
CPC ......... *A61M 1/0031* (2013.01); *A61M 1/0025* (2014.02); *A61M 16/044* (2013.01); *A61M 16/0459* (2014.02); *A61M 16/0463* (2013.01); *A61M 16/0465* (2013.01); *A61M 16/0479* (2014.02); *A61M 1/0056* (2013.01); *A61M 25/0113* (2013.01); *A61M 2025/0019* (2013.01); *A61M 2202/0208* (2013.01); *A61M 2205/3331* (2013.01); *A61M 2205/3334* (2013.01); *A61M 2205/3569* (2013.01); *A61M 2205/3592* (2013.01); *A61M 2205/505* (2013.01); *A61M 2209/10* (2013.01); *A61M 2210/1035* (2013.01); *A61M 2230/42* (2013.01)

(58) Field of Classification Search
None
See application file for complete search history.

(56) References Cited

U.S. PATENT DOCUMENTS 5,819,723 A * 10/1998 Joseph .............. A61M 16/0479
                                                            128/202.22
6,440,061 B1 * 8/2002 Wenner ................ A61B 1/3132
                                                            600/114

(Continued)

FOREIGN PATENT DOCUMENTS

| JP | 2008264212 A | 11/2008 |
|---|---|---|
| KR | 20070033024 A | 3/2007 |

(Continued)

*Primary Examiner* — Bradley Philips
*Assistant Examiner* — Eric Bryant

(57) ABSTRACT

Disclosed is a suction device. The suction device includes a sensor unit which measures a breathing condition of a patient, a tube unit which is inserted into a bronchus of the patient in order to suck foreign material generated in the bronchus of the patient, when the values measured by the sensor unit exceeds a predetermined reference value, and a control unit which controls to drive the tube unit based on the measured value received from the sensor unit. According to the present invention, there is provided the suction device which is automatically operated by directly determining whether foreign material is generated in the bronchus of the patient.

23 Claims, 9 Drawing Sheets

(56) References Cited

U.S. PATENT DOCUMENTS

| | | | | |
|---|---|---|---|---|
| 6,889,688 B1* | 5/2005 | Wright | B65H 75/406 128/200.24 |
| 7,503,328 B2* | 3/2009 | Kolobow | A61M 16/0463 128/200.26 |
| 7,621,898 B2* | 11/2009 | Lalomia | A61M 1/0005 119/14.46 |
| 2002/0170556 A1* | 11/2002 | Gaitini | A61M 16/0409 128/200.14 |
| 2005/0126578 A1* | 6/2005 | Garrison | A61H 9/0078 128/874 |
| 2008/0236577 A1* | 10/2008 | Power | A61B 17/3474 128/203.12 |
| 2009/0156952 A1* | 6/2009 | Hunter | A61M 16/209 600/538 |
| 2009/0240199 A1* | 9/2009 | Rahimsobhani | A61M 16/04 604/101.02 |
| 2010/0152600 A1* | 6/2010 | Droitcour | A61B 5/05 600/534 |
| 2010/0324483 A1* | 12/2010 | Rozenberg | A61M 16/045 604/98.01 |
| 2011/0040359 A1* | 2/2011 | Harris | A61F 7/12 607/105 |
| 2013/0014761 A1* | 1/2013 | Elia | A61M 16/04 128/207.15 |
| 2013/0030411 A1* | 1/2013 | Kreck | A61F 7/12 604/514 |
| 2013/0267892 A1* | 10/2013 | Woolford | A61M 3/0258 604/34 |
| 2013/0324917 A1* | 12/2013 | Akagane | A61B 17/320092 604/35 |
| 2014/0246015 A1* | 9/2014 | Einav | A61M 16/0463 128/202.16 |

FOREIGN PATENT DOCUMENTS

| | | |
|---|---|---|
| KR | 20070065391 A | 6/2007 |
| KR | 20100000636 A | 1/2010 |
| KR | 101279451 B1 | 6/2013 |
| KR | 101403658 B1 | 6/2014 |

* cited by examiner

ARTIFICIAL INTELLIGENCE PORTABLE SUCTION DEVICE HAVING A CATHETER REEL

RELATED APPLICATIONS

This application claims priority to Korean Patent Application No. 10-2014-0023985, filed on Feb. 28, 2014 in the Korean Intellectual Property Office, the entire disclosure of which is incorporated herein by reference.

BACKGROUND OF THE INVENTION

1. Field of the Invention

The present invention relates to a suction device, and more specifically to an artificial intelligence type suction device which sucks in by automatically determining an occurrence of foreign material in a user's respirator and inserting a catheter.

2. Description of the Related Art

A medical suction device is a medical foreign material suction device which sucks in and removes by force into a container foreign materials such as blood, saliva, vomitus and secreta that are generated from an inside of a patient's body while operating on the patient in hospitals. In general, patients with impaired mobility at home or hospital have a suction device mounted constantly for a guardian or nurse to drain foreign material out of the trachea or surgical site.

A conventional suction device includes a suction unit for sucking foreign material or other waste, a containment unit for containing the foreign material, a driving unit for applying a suction force to the suction device and a suction tube through which waste flows. However, the conventional suction device needs an improvement in that the noise is loud and operation by the patient or guardian is necessary.

In addition, since foreign materials may be generated during sleep to block the trachea, the nurse, carer or guardian should operate the suction device from time to time. However, the conventional suction device is inconvenient since the foreign material in the patient's body should be frequently removed according to condition or reaction from the patient night and day. In addition, since expenses for the catheters that should be replaced due to contamination whenever foreign material is removed are high, a method which is capable of continuously using the catheter is required.

Relating to this, Korean Patent Registration No. 10-1403658 discloses a medical suction catheter including an on-off valve used for sucking foreign material in the body of the patient, and Korean Patent Registration No. 10-1279451 discloses a medical suction device which can automatically make sewage disposal of extracts. The techniques disclosed in the above patents have advantages such as being stable and hygienic in operation. However, these patents fail to disclose a technical configuration that provides convenience to the patient with impaired mobility.

Therefore, there is a need to develop a suction device for removing foreign material from the patient from time to time and enhancing convenience and work efficiency of the guardian or nurse in order to improve the health of patient with impaired mobility.

SUMMARY OF THE INVENTION

In consideration of the above-mentioned circumstances, it is an object of the present invention to provide a suction device which sucks foreign material by detecting the foreign material in a patient's bronchus itself to automatically insert the catheter into the patient.

In order to achieve the above object, a suction device according to one embodiment of the present invention includes a drive unit, an input unit, a sensor unit, a tube unit, a control unit, and a storage unit. The drive unit is disposed on the bottom of the suction device and is configured to periodically pump, the input unit is disposed on a front of the suction device and is configured to input setting values for control, the sensor unit is configured to measure a breathing condition of a patient, the a tube unit is configured to be inserted into a bronchus of a patient to suck foreign material generated in the bronchus when the foreign material is generated in the bronchus, and move out of the bronchus, the control unit is configured to receive the setting values and the measured results respectively transmitted from the input unit and the sensor unit and control the drive unit based on the received setting values and measured results; and the storage unit sucks and stores foreign material and stores and supplies saline water.

In one embodiment, the drive unit may include a brushless DC motor (BLDC motor) which sucks and injects air by periodical pumping, and a driver which is connected to the BLDC motor at a distance and receives a control signal transmitted from the control unit to control the BLDC motor.

In one embodiment, the input unit may include: a breathing information display window in which a user's respiration rate per minute, a single respiratory air volume showing a volume breathed by a user at one time and breathing information showing respiration rate per hour are displayed; and a device setting window in which setting buttons for operating a simple respiratory function and suction are provided.

In one embodiment, the sensor unit may include: a mass flow meter (MFM sensor) which is configured to detect a daily breathing condition showing a patient's breathing pattern and a volume of exhaled gas for a predetermined time, and transmits the detected results to the control unit, and measure a mass of a patient's exhaled gas and the daily breathing condition and transmit the measured results of the daily breathing condition to the control unit.

In one embodiment, the control unit may be configured to analyze the daily breathing condition received from the MFM sensor, and if it is determined that foreign material is generated in the body of the patient, control the drive unit to suck the foreign material, and analyze the daily breathing condition received from the MFM sensor, and if it is determined that the user's breathing condition is irregular and difficult, control to drive the simple respiratory function.

In one embodiment, the tube unit may include: a catheter reel and a tube cover, and the catheter reel may include: a catheter which has a tube structure to suck foreign material; a screw frame which includes a plurality of protruded threads formed on an outer circumference thereof on which the catheter is reeled, and is configured to push or pull the catheter depending on the rotation direction thereof; a catheter reel case which includes a plurality of holes into which saline water for cleaning the catheter surface is injected formed therein, and houses the catheter and the screw frame; and a stepping motor configured to rotate the screw frame, wherein the tube cover may be formed outside of the catheter so that the catheter provides passages which are connected to a filter, the MFM sensor, a saline water container and a nebulizer between the bronchus and catheter reel.

In one embodiment, the suction device may further include: a motor cover which encloses the BLDC motor to prevent a noise of the BLDC motor from being leaked to an outside and reduce a vibration of the BLDC motor.

In one embodiment, the tube unit may further include: a T tube, and the T tube may include: a first cuff which is formed on an upper portion, and is inflated by air to expand the bronchus; a second cuff which is formed adjacent to and below the first cuff, and is inflated by air when the first cuff is deflated to expand the bronchus; a third cuff which is connected to the first cuff so as to flow air; a second tube which is connected to the second cuff so as to flow air; a first tube which sucks foreign material formed in the upper portion of the first cuff; and a fourth tube which, when the first cuff is deflated to make the second cuff inflate so that foreign material is formed in the upper portion of the second cuff, sucks the foreign material.

In one embodiment, the first and second cuffs may be alternately inflated and deflated to expand the bronchus of the user.

In one embodiment, the suction device may further include: a filter which prevents moisture from being penetrated into the sensor unit, and waste from being entered into the drive unit.

According to the present invention, since the suction device sucks foreign material only when an occurrence of foreign material is detected by determining the patient's daily breathing condition through a mass flow meter (MFM) unlike the conventional suction device, it is possible to reduce the pain of the patient and power consumption, and it allows use for an unconscious patient without a guardian.

In addition, since the motor cover provided in the suction device according to the present invention covers the brushless DC motor (BLDC motor) to prevent noises and vibrations generated from the BLDC motor from being leaked to an outside, a user environment that fits patients or infants who react sensitively to the ambient environment may be achieved.

Further, by pushing the emergency button provided in the suction device according to the present invention, the patient can call the guardian in a situation in which the suction device is not operating.

Further, it is possible to protect the patient by pushing the emergency button provided in the suction device according to the present invention when the device is operating abnormally, and the patient can call the guardian by pushing an emergency button connected to the suction device when the suction device is not operating.

Further, since the MFM sensor used in the present invention directly measures the invariable mass, it is possible to effectively measure gas with a low flow rate, and accurately measure the mass of flowing gas by directly measuring without the need to measure the volume or pressure of gas.

In addition, since the MFM sensor has no device generating a vibration during measuring the mass of gas, it is possible to increase the user's convenience during using the suction device according to the present invention.

Furthermore, since the suction device according to the present invention is provided with a simple respiratory function, it is possible to improve the pulmonary function through the simple respiratory function if the user's breathing condition is irregular or difficult, and save the user's life in the case of an emergency situation.

In addition, according to the present invention, improvement and training of a user's pulmonary function are possible through a function provided for the simple respiratory function whereby the user's inhalation time is subjected to increase gradually.

Further, according to the present invention, it is possible to reduce the maintenance costs since reuse is possible through saline irrigation to the catheter which has conventionally been the cause of high maintenance costs due to disposable single use for sanitary reasons present in the art.

Further, inflammation or infection of a user's bronchus may be minimized as the first and second cuffs of the tube unit provided in the suction device according to the present invention expand and contract alternately, and the tube unit has no need of frequent replacement, thereby user's convenience may be increased.

Further, by using the communication device such as the Bluetooth module or WiFi module provided in the suction device according to the present invention, the control unit can send a warning message to the guardian or medical team in the case of an abrupt change of the daily breathing condition of the user.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, the present invention will be described in detail with reference to the accompanying drawings.

Figure 1:
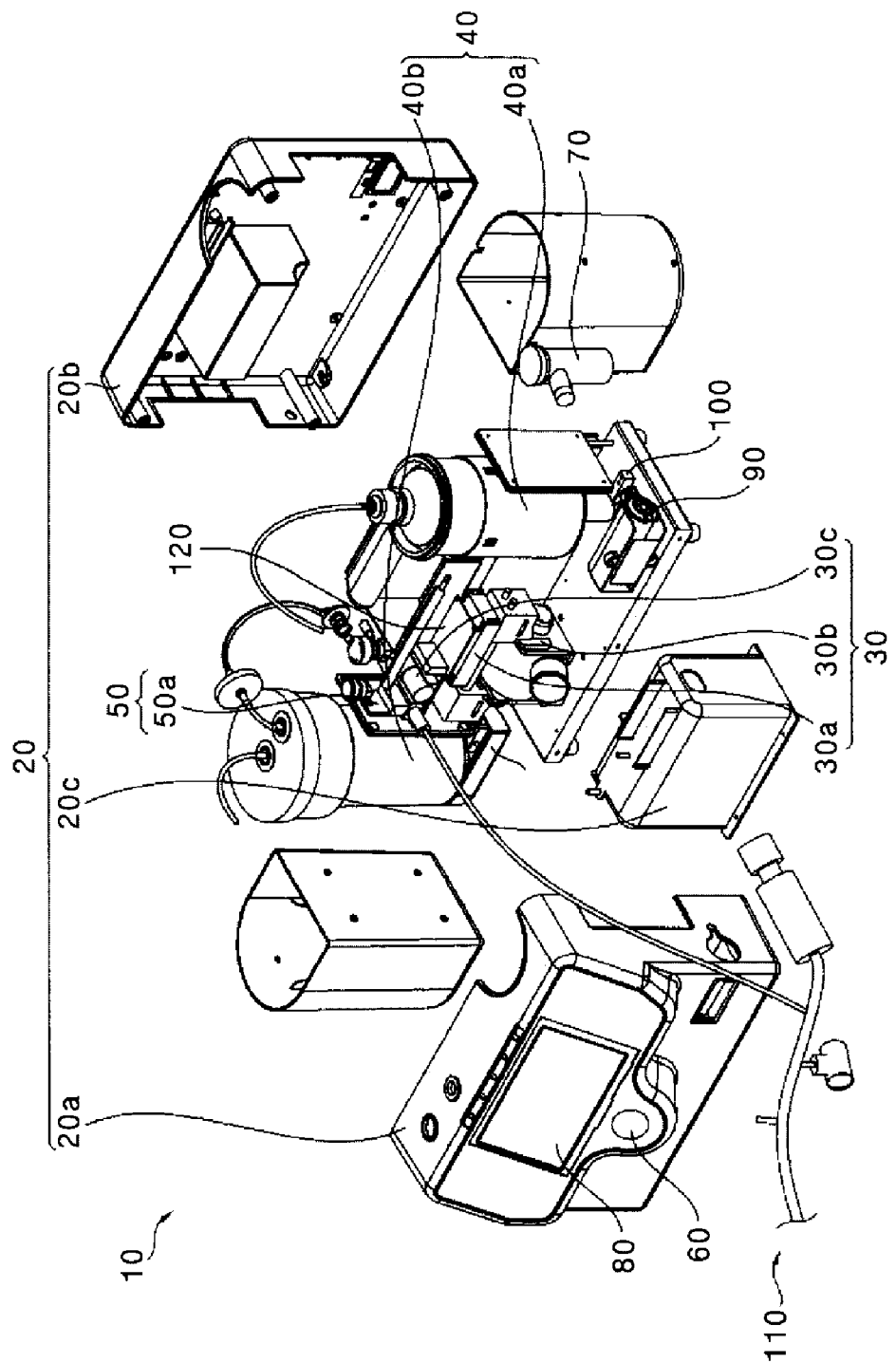
FIG. 1 is an exploded perspective view showing the structure of a suction device according to one embodiment of the present invention.

FIG. 1 is an exploded perspective view showing the structure of a suction device according to one embodiment of the present invention. Referring to FIG. 1, a suction device 10 according one embodiment of the present invention includes a cover unit 20, a driving unit 30, a storage unit 40, a sensor unit 50, a vacuum gauge 60, a nebulizer 70, an input unit 80, a filter 90, a scale 100, a tube unit 110 and a control unit 120.

The cover unit 20 includes a front cover 20a, a rear cover 20b and a motor cover 20c. The front cover 20a is provided with the input unit 80, and a switch for turning on and off the power of the suction device 10 on the top thereof.

The driving unit 30 includes a driver 30a, a brushless DC motor (BLDC motor) 30b and a solenoid valve 30c. The storage unit 40 includes a saline water container 40a and a suction container 40b. The sensor unit 50 includes a mass flow meter (MFM) sensor 50a.

The rear cover 20b is disposed on a rear of the suction device 10 and is coupled with the front cover 20a to protect the inner components of the suction device 10, while preventing noises from being leaked to an outside and external contaminants from entering therein.

The motor cover 20c is formed in a double-case structure with a sponge attached on the center thereof. The double-case structure is formed to absorb noise and reduce vibration generated from the driving unit 30. The motor cover 20c may reduce the stress for a user who uses the suction device 10 at all times due to the noise and vibration.

The driver 30a sends a signal received from the control unit 120 to control the BLDC motor 30b. The driver 30a is connected to the BLDC motor 30b with a cable at a distance to reduce the effects of heat and noise from the BLDC motor 30b, and is formed at the outside of the motor cover 20c.

The BLDC motor 30b is connected to the driver 30a so as to stably and periodically pump. The BLDC motor 30b is mounted on a lower end of the suction device 10 and provides power for suction of foreign material in the user's body and the respiration of the user. In the present invention, the BLDC motor 30b is used as the motor for driving the suction device 10.

Since the BLDC motor 30b, unlike the conventional AC motor, can easily change the pressure desired by the user, as well as a flow rate (NL/m) and driving cycle of the motor by increasing or decreasing an electric current, the suction device 10 according to the present invention can make selective suction driving possible only when foreign material is generated, without making continuous suction driving regardless of whether there is foreign material or not.

Further, the BLDC motor 30b has technical advantages such as excellent heat resistance, decreased noise, as well as no arc generation especially at the time of on/off. Therefore, not only is the motor life increased by about three times that of an AC motor but also it may be made in a small size.

Meanwhile, in one embodiment of the present invention, a waste-preventing filter may be mounted on the driving unit 30 to prevent contamination by the waste entering in backflow through a catheter 113a.

The solenoid valve 30c is provided with a bar for blocking the passage in an inner passage thereof, and when an electric current is applied to the coil provided in the solenoid valve 30c, the cylindrical metal rod in the coil is moved upward by an electromagnetic force to push the bar upward, so that the solenoid valve 30c is opened.

Meanwhile, when the supply of the electric current to the coil is cut off to make the cylindrical metal rod move downward, the bar descends by gravity to close the valve.

When inhaling foreign material, the control unit 120 controls the solenoid valve 30c to be closed, so that air including the oxygen being supplied to the user is prevented from being sucked into the suction device 10 again.

The solenoid valve 30c may be connected to all of the MFM sensor 50a, the saline water container 40a and the suction container 40b, or may be formed into three independent valves connected respectively to the MFM sensor 50a, the saline water container 40a and the suction container 40b.

For convenience of the description, the present invention will be described by dividing into the first to third solenoid valves 30c connected respectively to the MFM sensor 50a, the saline water container 40a and suction container 40b.

The storage unit 40 includes the saline water container 40a and the suction container 40b. The saline water container 40a is filled with saline water, and is fabricated in a proper size so as to secure space for the scale 100 in the lower portion thereof. The saline water container 40a includes its own motor so as to send saline water before inhaling foreign material to make the foreign material easily inhalable. The saline water container 40a may be detachably attached for the exchange and cleaning of saline water.

The saline water container 40a is provided with the scale 100 and a small motor in the lower portion thereof. The scale 100 constantly measures a weight of saline water in the saline water container 40a, and if the weight is decreased from a predetermined value, sends a signal to the control unit 120. The control unit 120 receives the signal and indicates a saline water supply signal through the input unit 80.

The saline water container 40a is connected to the first solenoid valve 30c. Thus, the first solenoid valve 30c is opened before foreign material is inhaled, and the saline water in the saline water container 40a is mixed with foreign material inside the user's bronchus to increase the fluidity of foreign material.

In addition, the saline water container 40a is connected to the catheter 113a to be inserted into the bronchus of the user, and pumps saline water into the catheter 113a by using its own motor, so as to sterilize and clean the catheter 113a.

The suction container 40b is formed inside the side of the suction device 10 and stores foreign material sucked in. The scale 100 is disposed in the lower portion of the suction container 40b. The suction container 40b is formed in a suitable volume which is large enough to secure a space for the scale 100. The suction container 40b may be detachably attached for treatment and cleaning of foreign materials.

The suction container 40b is coupled with the second solenoid valve 30c. Thus, if the fluidity of foreign material is increased by the saline water in the saline water container 40a, the first solenoid valve 30c is closed. Foreign material is sucked in with the second solenoid valve 30c opened.

When foreign material is sucked in, the second solenoid valve 30c is closed, and the third solenoid valve 30c connected to the MFM sensor 50a is opened. The sensor unit 50 includes the MFM sensor 50a.

The MFM sensor 50a is mounted on the side of the BLDC motor 30b, and since it has a small size and weight, the effect on the whole weight of the suction device 10 is insignificant. The MFM sensor 50a makes the mass of gas as a reference of measuring. Since the MFM sensor 50a directly measures an invariable mass, it is possible to exactly detect the flow rate of gas without requiring a complicated calculation.

Further, the MFM sensor 50a may effectively measure the gas with a low flow rate, and since the sensor is not configured to measure the volume or pressure of gas, it is possible to exactly measure the mass of flowing gas. In addition, since the MFM sensor 50a has no device generating a vibration during measuring the mass of gas, it is possible to increase the user's convenience during using the suction device 10.

The MFM sensor 50a can measure the mass of a variety of gases such as $CO_2$, Ar, methane, hydrogen, nitrogen, or the like. Specifically, by detecting the mass of $CO_2$ from the respiration of a patient who uses the suction device 10, and measuring complex data such as user's blood circulation, exhalation, inhalation, vital lung capacity and pulmonary function, it is possible to determine the condition of the user.

Thus, since the suction device 10 is provided with the MFM sensor 50a, it is possible to secure information on the unstable breathing condition due to aggravation of a patient's physical condition. Further, the MFM sensor 50a can measure information on a patient's daily breathing condition as well. Herein, daily breathing condition information includes information on the general state of a user's breathing condition such as the mass of air the user breathes in and out (inhalation mass and exhalation mass) or the flow rate and the respiration rate per minute.

Meanwhile, if foreign material is generated in the user's bronchus, the mass or flow rate of the air exhaled by the user becomes different. The MFM sensor 50a detects values of the changed user's inhalation mass, exhalation mass or the flow rate and the results of the respiration rate per minute, and sends to the control unit 120. The control unit 120 can determine such a changed state depending on the values detected by the MFM sensor 50a.

Meanwhile, in one embodiment of the present invention, a pressure sensor such as a sound pressure sensor that measures the size of user's groan may be used instead of using the MFM sensor 50a. Commonly, a patient who feels uneasy due to foreign material generated in his bronchus groans unwittingly and in the case of using a sound pressure sensor, the level of the patient's groan is detected by the MFM sensor 50a and sent to the control unit 120, so that it is possible to control taking the patient's subjective condition into consideration.

Meanwhile, in one embodiment of the present invention, it is preferable that the sensor unit 50 is provided with a filter for preventing moisture from entering into the sensor unit 50.

Preferably, the vacuum gauge 60 is mounted on the front of the front cover 20a in order to show the suction pressure of the suction device 10. If the suction pressure of the suction device 10 increases abnormally, it could damage the respiratory organ of the user. Therefore, it is preferable to mount the vacuum gauge 60 on the front so as to confirm whether there is normal pressure or not. Meanwhile, in one embodiment of the present invention, it is preferable that an analog vacuum gauge that is safe and has less error is used for the vacuum gauge 60.

The nebulizer 70, which is mounted outside of the side of the suction device 10, provides humidity to the patient's trachea if the user has difficulty in breathing, so as to stabilize the breathing condition of the user.

The input unit 80 is provided with a panel-type display, and it is preferable that a plurality of buttons are arranged at a position in which the input unit 80 is disposed so that selection of respiration steps by age is possible. Since the input unit 80 is embodied in a touch panel type display, the user can select intuitively, thereby it has an advantage that there is no need to pay extra attention to the description of the operating method that is not easy to understand.

The filter 90 is mounted on the front of the saline water container 40a to purify the air entering into the body of the user.

The scales 100 are mounted below the saline water container 40a and the suction container 40b to measure the weights of foreign materials and saline water in the saline water container 40a and the suction container 40b.

When the measured value of the scale 100 installed below the saline water container 40a is less than a predetermined reference value, the scale 100 sends an underweight signal representing underweight of the saline water to the control unit 120, and the control unit 120 outputs a saline water replenish request message through a touch panel type display or speaker of the input unit 80.

Meanwhile, when the measured value of the scale 100 installed below the suction container 40b exceeds a predetermined reference value, the scale 100 sends an overweight signal representing overweight of the saline water to the control unit 120, and the control unit 120 outputs a foreign material deplenish request message through the touch panel type display or speaker of the input unit 80.

The tube unit 110 is connected to the outside of the suction device 10 to suck in foreign material generated in the bronchus of the user.

The control unit 120 is mounted on the driver 30a. The control unit 120 analyzes the daily breathing condition information received from the MFM sensor 50a, and sends a signal for driving the BLDC motor 30b by the driver 30a depending on the analysis results. The BLDC motor 30b starts pumping through the signal received from the driver 30a, and the tube unit 110 sucks in foreign material generated in the bronchus of the user.

Figure 2:
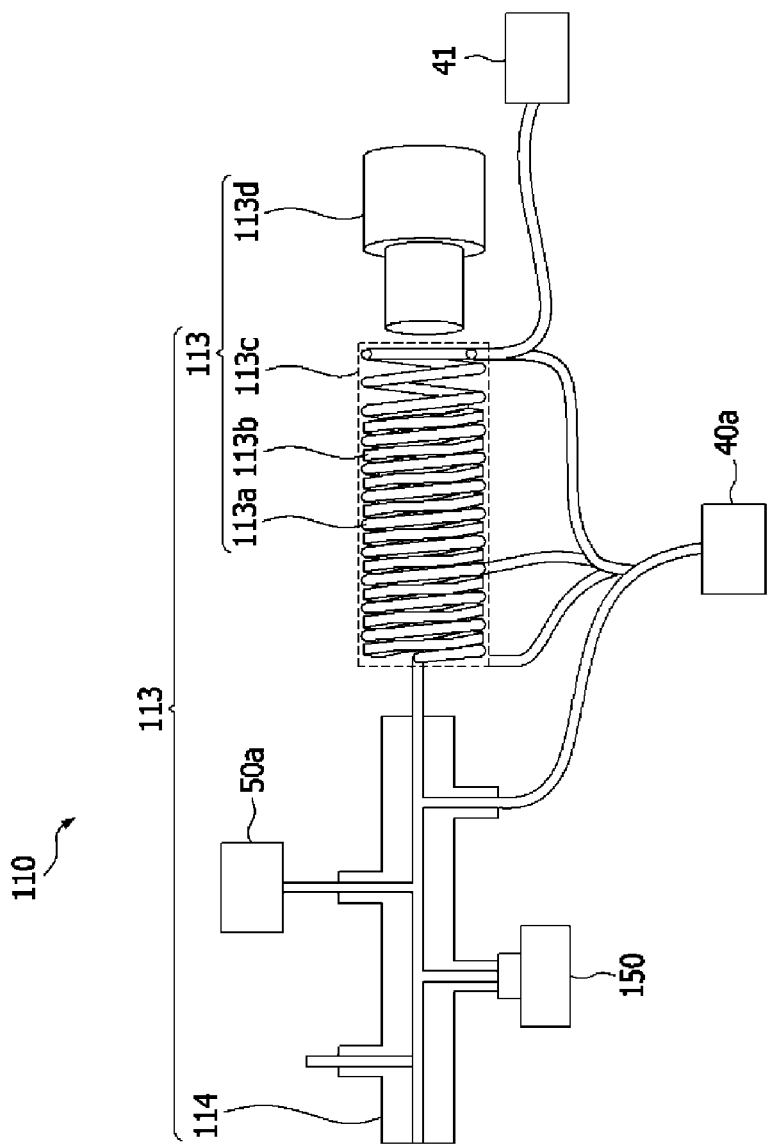
FIG. 2 is a perspective view showing the structure of a tube unit included in the suction device according to one embodiment of the present invention in FIG. 1.

FIG. 2 is a perspective view showing the structure of the tube unit included in the suction device of FIG. 1. Referring to FIG. 2, the tube unit 110 includes a catheter reel 113 and a tube cover 114. The catheter reel 113 includes a catheter 113a, a screw frame 113b, a catheter reel case 113c, a stepping motor 113d, and a waste can 41.

The catheter 113a is reeled between protruded threads of the screw frame 113b, and moves out of the catheter reel 113 or returns into the catheter reel 113 again depending on the rotation direction of the screw frame 113b.

That is, when the screw frame 113b coupled with the stepping motor 113d rotates by the rotation of the stepping motor 113d, the threads formed in the catheter reel case 113c are meshed with the screw frame 113b to move in different (i.e. forward and reverse) directions depending on the rotation direction of the stepping motor 113d.

Thus, in the state in which the catheter 113a is reeled between protruded threads of the screw frame 113b, and tensile and frictional forces are applied between the catheter 113a and the screw frame 113b, when the screw frame 113b rotates by the rotation of the stepping motor 113d, the catheter 113a is moved in the rotation direction by the tensile and frictional forces applied thereto depending on the rotation direction of the screw frame 113b.

One end of the catheter 113a is disposed in the tube cover 114, and the other end is connected to the waste can 41 passing through the catheter reel 113. In addition, the tube cover 114, except portions connected to the catheter reel 113 and directed to the bronchus, has four protruded openings formed on outside so as to be respectively coupled with the MFM sensor 50a, the saline water container 40a, the nebulizer 70 and a filter 150.

Saline water moves into the catheter 113a through the protruded opening connected to the saline water container 40a, so as to sterilize and disinfect the inside of the catheter 113a and remove foreign materials.

In addition, three saline water hoses connected to the catheter reel case 113c transport saline water injected from the saline water container 40a to sterilize and clean the outer surface of the catheter 113a in the catheter reel case 113c and the screw frame 113b.

The filter 150 functions to purify air inletting from the outside. Alternately, after separating the filter 150 from the tube cover 114, an artificial respirator may be installed in the protruded opening connected to the filter 150. Thus, when a problem with the respirator of the patient has occurred during suction, the user may separate the filter 150 from the tube cover 114 and then connect the artificial respirator thereto so as to have the patient's respiratory function recovered.

Meanwhile, the MFM sensor 50a is connected to the front portion of the catheter 113a to measure the mass flow of the gas exhaled by the patient, and the control unit 120 analyzes the measured value received from the MFM sensor 50a to determine the bronchus condition of the patient, and based on the analysis results, the stepping motor 113d is driven to insert the catheter 113a into the patient's bronchus or draw it out of the patient's bronchus.

Figure 3:
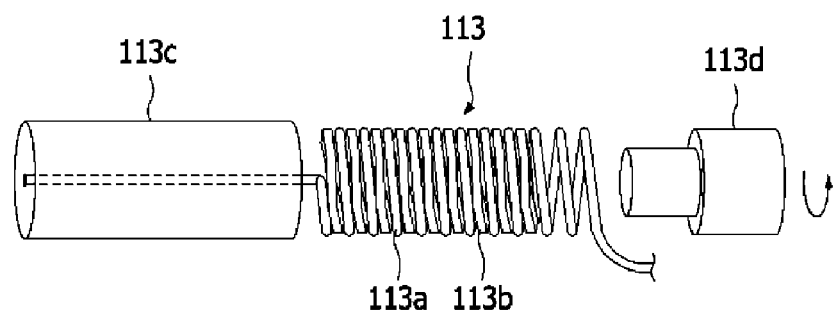
FIGS. 3 and 4 are exploded perspective views showing the structures of a catheter reel in FIG. 2.
Figure 4:
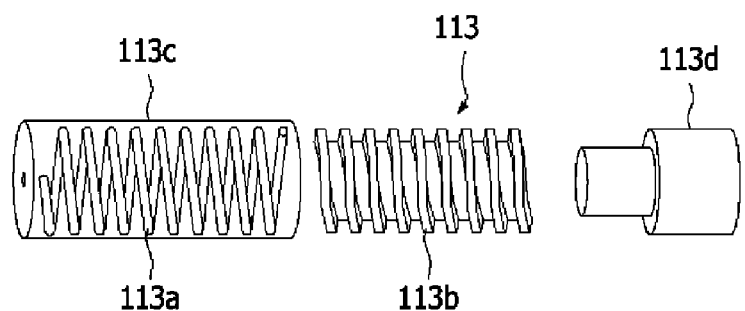

FIGS. 3 and 4 are exploded perspective views showing the structure of the catheter reel 113 included in the tube unit 110. Referring to FIGS. 3 and 4, the catheter reel 113 includes the catheter 113a, the screw frame 113b, the stepping motor 113d and the catheter reel case 113c.

The catheter 113a may be formed of innoxious silicon, rubber, or polymer having elasticity. The catheter 113a is reeled between the protruded threads of the screw frame 113b to be fixed thereto by the frictional and tensile forces.

The stepping motor 113d is coupled with the screw frame 113b, so as to be rotated by the rotation of the stepping motor 113d.

The stepping motor 113d may be rotated at minute angles, so as to gently insert the catheter 113a into the bronchus of the patient without damage to the bronchus. That is, since individual bronchi are different from person to person, when using the stepping motor 113d, it is possible to prevent or minimize a damage to the bronchus by individually adjusting and setting the depth of the catheter 113a meeting the bronchus of each patient.

The catheter 113a moves into the bronchus by the forwardly rotating stepping motor 113d to suck in foreign material, and is reeled onto the screw frame 113b and pulled by the reversely rotating stepping motor 113d in a direction opposite to the sucking.

During such a process, the surface of the catheter 113a is contaminated by foreign materials in the bronchus. In order to remove the foreign materials, the lower portion of the catheter reel case 113c is provided with three holes into which saline water hoses are inserted.

Referring to FIG. 2 and FIG. 3, when injecting saline water through the holes formed in the catheter reel case 113c, the injected saline water sterilizes and cleans the foreign materials remaining in the catheter 113a and the screw frame 113b. Further, in order to sterilize and clean the foreign materials existing in the catheter 113a, saline water moves to the waste can 41 passing through the catheter 113a.

Referring to FIG. 4, the screw frame 113b includes a plurality of protruded threads having a substantially rectangular cross-section formed on the outer circumference thereof, and the catheter 113a is reeled between the protruded threads. Further, the catheter 113a, the screw frame 113b, the catheter reel case 113c and the stepping motors 113d are respectively attached by an easy to assemble and detach structure, to effectively clean away the foreign materials.

Figure 5:
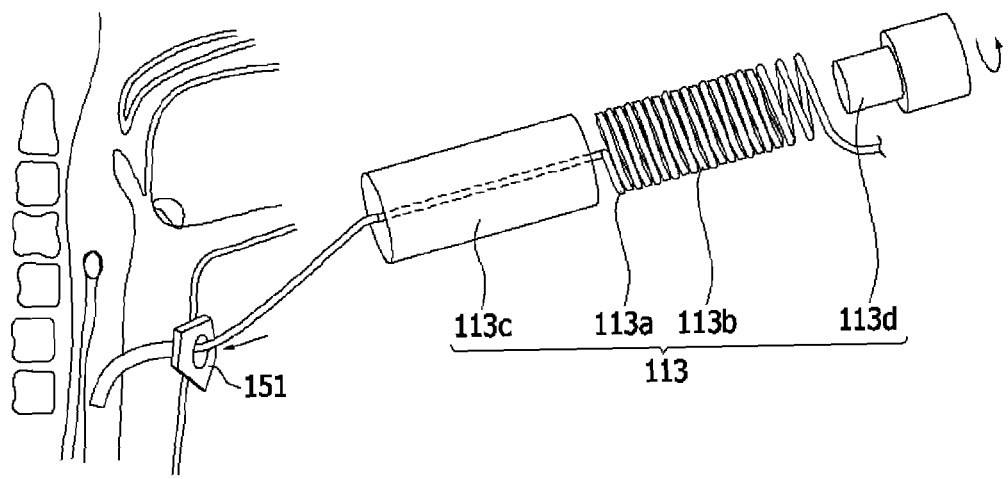
FIGS. 5 and 6 are exploded perspective views showing the operation in which the catheter reel of FIG. 2 is inserted into a bronchus through a T tube.
Figure 6:
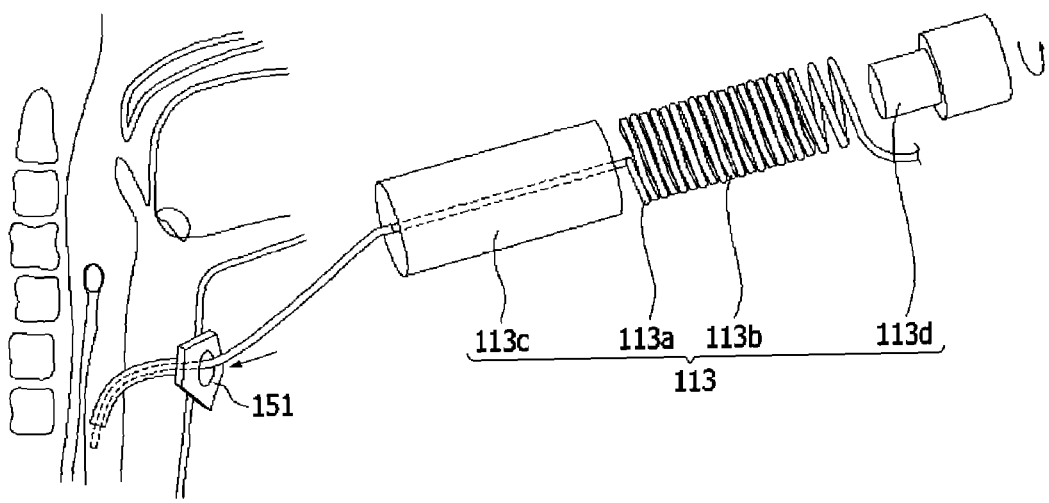

FIGS. 5 and 6 are exploded perspective views showing an operation in which the catheter reel 113 is inserted into the bronchus through a T tube 151. Referring to FIGS. 5 and 6, the sensor unit 50 detects the patient's daily breathing condition changed by the foreign materials in the bronchus, and the control unit 120 controls to drive the stepping motor 113d based on the detected results.

When the stepping motor 113d rotates, the catheter 113a is inserted into the patient's bronchus through the T tube 151. At this time, the catheter 113a is gently inserted by the minutely rotating stepping motor 113d so as to prevent a damage do the bronchus of the patient. At this time, various types of T tube 151 suiting the patient may be used based on the condition of the patient.

In addition, the control unit 120 injects saline water in the storage unit 40 through the catheter 113a, so that the foreign materials adsorbed to the bronchus are changed into a colloidal state which is likely to be detached. At this time, the control unit 120 controls to drive the BLDC motor 30b to suck the foreign materials in an easily suckable state through the catheter 113a.

After the catheter 113a is inserted into the bronchus to suck in the foreign materials, it is reeled onto the screw frame 113b by the reversely rotating stepping motor 113d to move out of the bronchus.

When the catheter 113a that was inserted into the bronchus is reeled onto the screw frame 113b, saline water is injected by pumping of the BLDC motor 30b through the holes formed outside of the catheter reel case 113c to clean the outside of the catheter 113a.

In addition, saline water is also injected into the catheter 113a by the pumping of the BLDC motor 30b to clean the foreign material remaining in the catheter 113a as well.

As described above, according to the present invention, by cleaning the inside and outside of the catheter 113a, it is possible to prevent damage to the bronchus due to contamination of the catheter 113a. Further, by maintaining and managing the catheter 113a, which is conventionally only disposably used for sanitary reasons, in a state reusable for at least one day, it is possible to reduce costs arising from frequent replacement of the catheter 113a.

Figure 7:
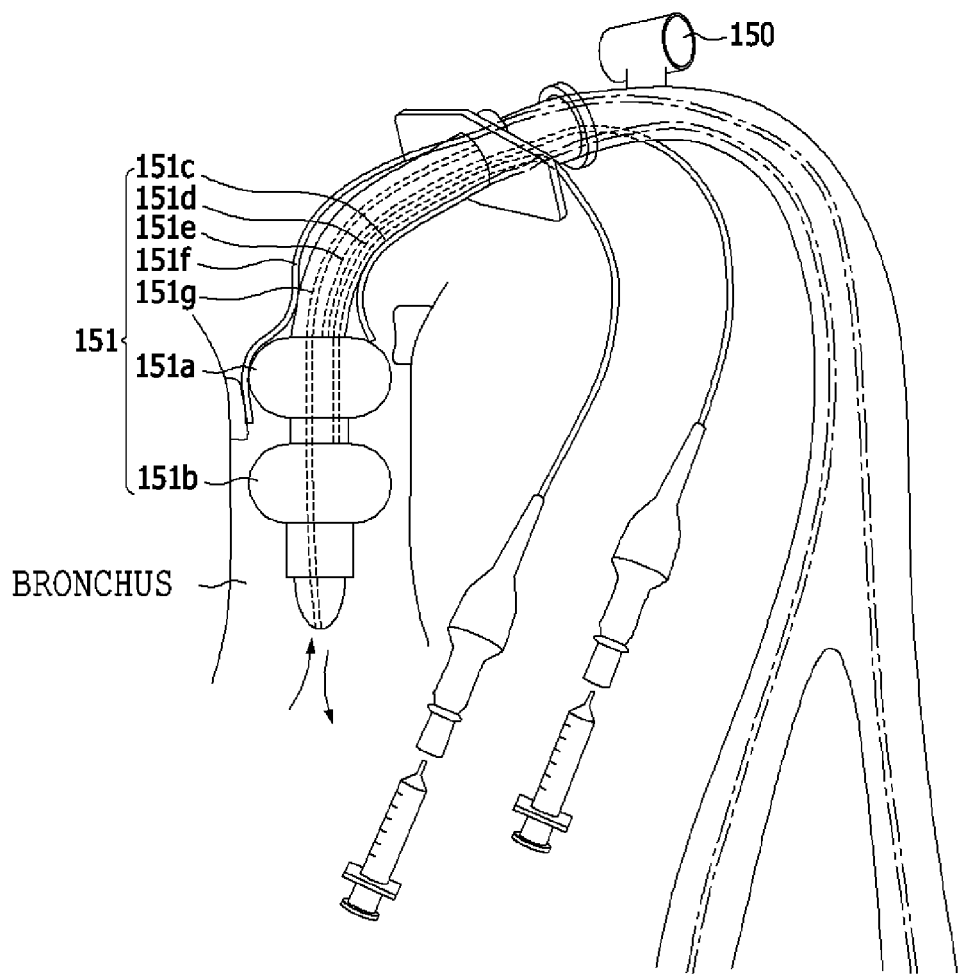
FIG. 7 is a perspective view showing the structure of the T tube that may be connected to the tube unit included in the suction device according to one embodiment of the present invention in FIG. 1.

FIG. 7 is a perspective view showing the structure of the T tube that may be connected to the tube unit included in the suction device of FIG. 1.

Referring to FIG. 7, the T tube 151 includes a first cuff 151a, a second cuff 151b, a first tube 151c, a second tube 151d, a third tube 151e, a fourth tube 151f and a fifth tube 151g.

The T tube 151 is connected to the suction device 10, and includes the first and second cuffs 151a and 151b. The T tube 151, which is a tube for tracheostomy, is disposed inside the user's bronchus passing through the user's neck. The first and second cuffs 151a and 151b of the T tube 151 are inflated by syringe or air injector in the user's bronchus to perform the function of expanding the inside of the bronchus.

The first and second cuffs 151a and 151b are inflated one after another at a predetermined interval of time in the user's bronchus. Meanwhile, the first and second cuffs 151a and 151b are inflated and deflated alternately one after another at the upper and lower positions. The reason is that, if the first and second cuffs 151a and 151b are continuously maintained in an inflated state, inflammation or infection may occur in the bronchus.

Thus, in the present invention, it is possible to prevent an occurrence of the inflammation or infection in the bronchus by inflating and deflating the first and second cuffs 151a and 151b one after another at an interval of time.

Meanwhile, in order to inflate the first and second cuffs 151a and 151b alternately one after another, the third tube 151e and the second tube 151d are independently connected to the first and second cuffs 151a and 151b.

Specifically, after a predetermined time has elapsed from when the first cuff 151a is inflated, air is drawn out using the third tube 151e, and air is inlet into the second cuff 151b to inflate it by using the second tube 151d. By repeatedly performing the above-described operation at a predetermined interval of time, the possibility of causing inflammation or infection to the user's bronchus is reduced, and a need for the user to exchange the T tube 151 frequently is removed, such that convenience may be increased.

Meanwhile, in order to reduce a load applied to the neck of the user, it is preferable that, with a long tube being firstly connected, the long T tube 151 is connected to the tubes of the suction device 10.

Also, the long T tube is provided with the first tube 151c and the fourth tube 151f therein, which extend outward from the suction device 10 and reach the bronchus of the user.

Meanwhile, when the MFM sensor 50a detects the user's daily breathing conditions such as the respiration rate per minute, as well as the mass and flow rate of exhaled gas and sends a signal representing the detected results to the control unit 120, then the control unit 120 determines the patient's condition based on the received signal. If it is determined that there is a problem with the patient's breathing condition depending on the analysis of the daily breathing condition, the control unit 120 controls to drive the BLDC motor 30b to supply oxygen through the third tube 151e.

Further, in one embodiment of the present invention, by providing the control unit 120 with wireless communication devices such as a Bluetooth module or WiFi module, it is possible to provide simple artificial respiration through the fifth tube 151g when the daily breathing condition is rapidly changed, and at the same time an alert message may be sent to the guardian or medical team.

Meanwhile, the first tube 151c and the fourth tube 151f are passages for sucking foreign materials generated in the patient's bronchus. The first tube 151c sucks in foreign material that may be formed in the upper portion of the first cuff 151a while the first cuff 151a is inflated, and the fourth tube 151f sucks in foreign material that may be generated in the upper portion of the second cuff 151b while the second cuff 151b is inflated with the air from the first cuff 151a which is subsequently deflated.

Thus, while the first cuff 151a or the second cuff 151b is inflated by the first tube 151c and the fourth tube 151f, foreign materials generated in the bronchus are sequentially sucked.

The saline water of the saline water container 40a is atomized into fine particles through the first tube 151c and the fourth tube 151f on the foreign materials generated in the body such as saliva, sputum or solid impurities. When saline water is atomized on the foreign material, fluidity of the foreign material is increased. Therefore, the foreign material is easily sucked in by the suction force applied through the first tube 151c and the fourth tube 151f.

That is, in the present invention, before the suction device 10 sucks in, saline water is firstly mixed with foreign material through the first tube 151c and the fourth tube 151f so as to increase the fluidity of the foreign material, and the BLDC motor 30b drives to suck in the foreign material.

Figure 8:
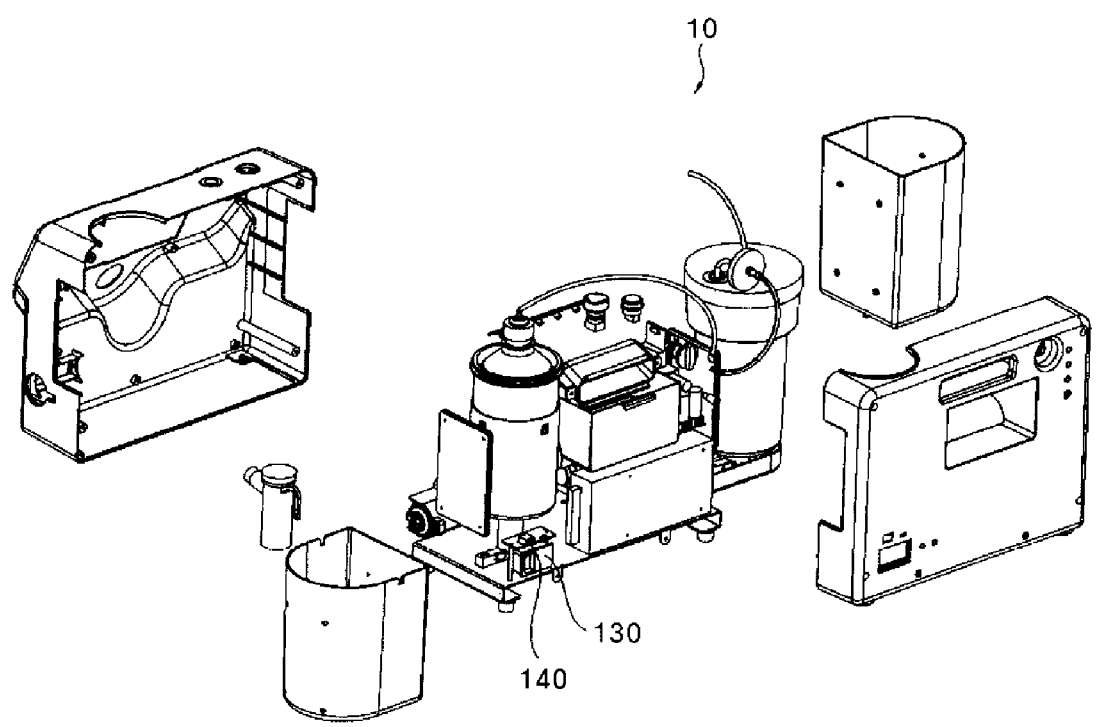
FIG. 8 is an exploded perspective view showing the structure of the suction device according to one embodiment of the present invention in FIG. 1 as seen from a different direction thereof.

FIG. 8 is an exploded perspective view showing the structure of the suction device of FIG. 1 as seen from a different direction thereof. As shown in FIG. 8, in one embodiment of the present invention, the suction device 10 may be additionally provided with a USB terminal 140 and a power switch 130 on the rear thereof.

The USB terminal 140 is connected to an external device such as a notebook or a desktop PC, and is used to transmit a user's daily breathing condition information to the external device in real time, so that the external device may store or make statistical analysis on the daily breathing information.

Meanwhile, the power switch 130 is disposed below the USB terminal 140, and is used to turn on and off the power of the suction device 10.

Figure 9:
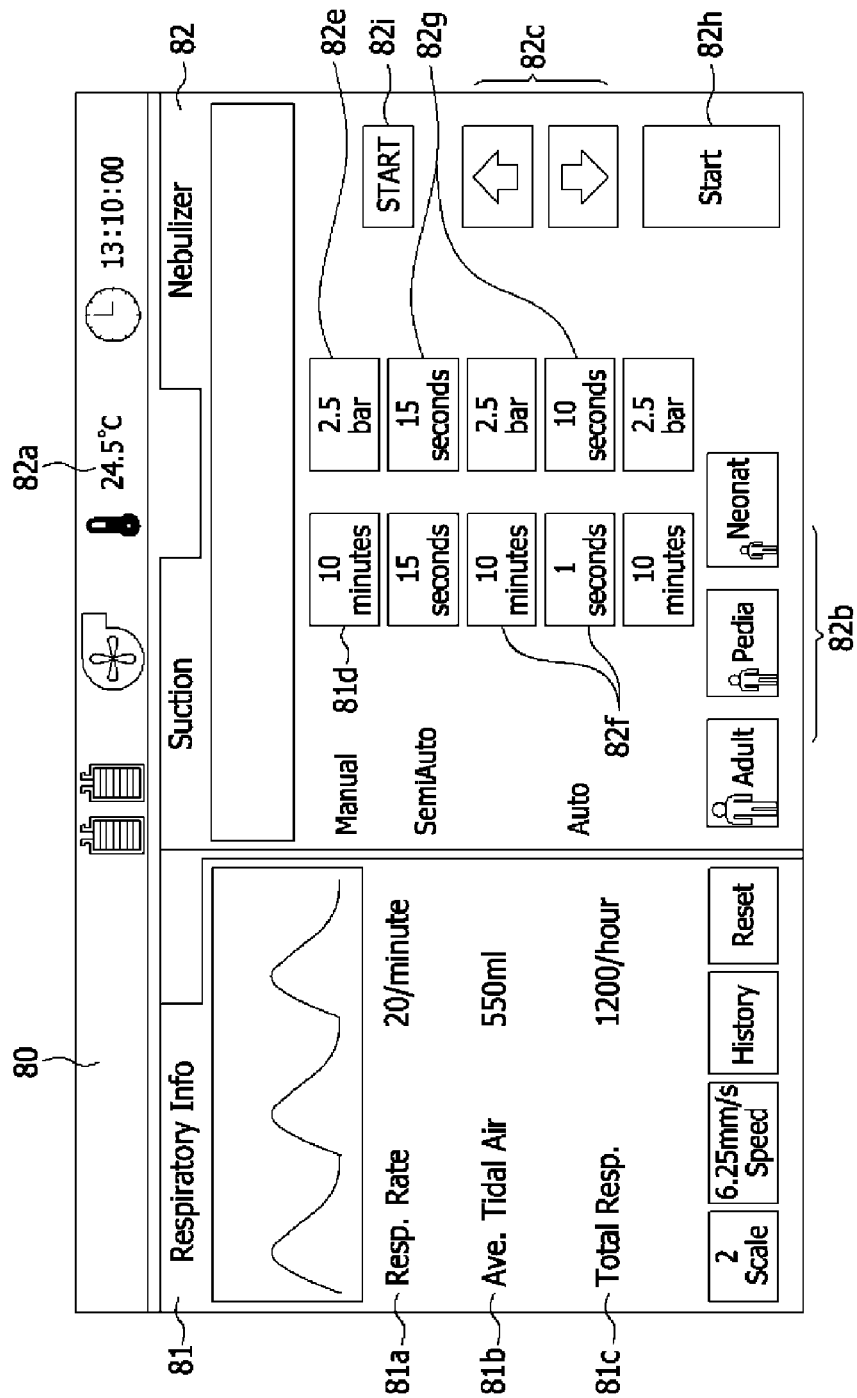
FIG. 9 is a view showing an example of an operation screen displayed on an input unit of the suction device according to one embodiment of the present invention in FIG. 1.

FIG. 9 is a view showing an example of an operation screen displayed on the input unit 80 of the suction device of FIG. 1. As shown in FIG. 9, the suction device 10 according to the present invention may be additionally provided with a nebulizer function that can improve the pulmonary function for improvement of a user's respiratory function.

The nebulizer function is a function for inducing the user's exhalation and inhalation time to be gradually increased. Specifically, for improvement of patient's respiratory function, the nebulizer 70 is used, or an additional nebulizer may be used by connecting it to the tube unit 110 after separating the nebulizer 70.

When using the additional nebulizer, the user may recover to normal conditions from conditions of irregular respiration rate per minute and an abnormally high respiration rate with his or her vital lung capacity improved.

Meanwhile, referring to FIG. 9, a touch panel type display included in the input unit 80 may be largely divided into a breathing information display window 81 and a device setting window 82. The breathing information display window 81 displays a respiration rate per minute 81a, single respiratory air volume 81b and respiration rate per hour 81c. The device setting window 82 is provided with a room temperature setting button 82a, respiration rate step setting buttons 82b, adjustment buttons 82c, an operation time setting button 82d, a pressure setting button 82e, inhalation time setting buttons 82f, exhalation time setting buttons 82g, a start button 82h, and a simple respiration button 82i.

The respiration rate per minute 81a shows a sum of exhalation and inhalation per minute, and the single respiratory air volume 81b shows the volume of air breathed out or in during exhalation or inhalation. The respiration rate per minute 81a and the single respiratory air volume 81b are numerical values measurable in a short time of one minute or less from the user.

The respiration rate per hour 81c shows a sum of exhalation and inhalation per hour, and is a numerical value for confirming whether the patient's condition is improving or not.

The room temperature setting button 82a shows the current room temperature of the place where the user uses the suction device 10, and it is an important factor in the case for improving the operating room or the condition of the user with a weak bronchus.

The respiration rate step setting button 82b includes a plurality of buttons, and the user selects the respiration rate step depending on his or her respiration rate per minute 81a. When selecting any one of the respiration rate step setting buttons 82b, air is injected at a rate equivalent to the half of the user's respiration rate per minute 81a.

For example, when the user selects 10 as the respiration rate per minute using the respiration rate step setting button 82b, the nebulizer injects 5 times for one minute. Therefore, the nebulizer injects 5 times matching with exhalation for 6 seconds at one time.

Thus, the user is inhaling while air is injected by the nebulizer function of the suction device 10, and whenever the respiration rate step is increased, the exhalation time is gradually increased so as to improve vital lung capacity, and the irregular and abnormally long respiration rate per minute may be recovered to normal.

Meanwhile, in one embodiment of the present invention, the number of the respiration rate step setting button 82b is not limited to three, and a plurality of buttons exceeding three may be provided.

The adjustment button 82c is a button for inputting the setting of pressure, time, etc., and the operation time setting button 82d is a button for starting the operation of the suction device 10 with the setting completed.

The operation time setting button 82d is a button for setting the time at which the user uses the suction device 10, and the user can input the service time of the suction device 10 in minutes by using this button The pressure setting button 82e is a button for setting the pressure of air atomized by the respirator of the user, and the user can freely set the pressure within a predetermined range by using this button.

The inhalation time setting button 82f is a button for setting inhalation time, which is the time for the user to breathe in, and the user can set his or her inhalation time in seconds within the range of 1 second to 10 seconds by using this button.

The exhalation time setting button 82g is a button for setting exhalation time, which is the time for the user to breathe out, and the user can set his or her exhalation time in seconds within the range of 1 second to 10 seconds by using this button.

The start button 82h is a button for the user to start the operation of the suction device 10 after completing the setting for operation on the device setting window 82.

The simple respiration button 82i is a button for manual operation when improving a user's breathing condition or when a user's breathing condition is irregular and difficult. However, in the suction device 10 according to the present invention, basically the MFM sensor 50a measures a user's breathing condition to start simple respiration by artificial intelligence.

Thus, the simple respiration button 82i is used to increase a user's inhalation time and improve his or her pulmonary function or during an emergency.

TABLE 1

| Respiration rate step (by age) | Respiration rate per minute (time/min) |
|---|---|
| Adult(Over 18 yrs) | 10 |
| Adolescent(12~18 yrs) | 15 |
| Children(5~12 yrs) | 20 |
| Preschooler(4~5 yrs) | 25 |
| Toddler(1~3 yrs) | 30 |
| Infants(1 month~1 yrs) | 40 |
| Newborn(0~1 month) | 50 |

TABLE 2

| | Flow rate increase step (min) | | | | | | | | | |
|---|---|---|---|---|---|---|---|---|---|---|
| | 1 | 2 | 3 | 4 | 5 | 6 | 7 | 8 | 9 | 10 |
| Injection time rate | 1 | 1.1 | 1.2 | 1.3 | 1.4 | 1.5 | 1.6 | 1.7 | 1.8 | 1.9 |
| Pressure ($kg/cm^2$) | 2.5 | 2.5 | 2.5 | 2.5 | 2.5 | 2.5 | 2.5 | 2.5 | 2.5 | 2.5 |

Table 1 shows the respiration rate per minute 81a in the respiration rate step setting button 82b divided by age, and Table 2 shows the injection time rate and pressure according to the flow rate increase steps.

Data in Table 1 and Table 2 are inputted in the suction device 10 according to the present invention as basic information, and the numerical values listed in Table 1 and Table 2 may be freely changed by the user through the input unit 80.

Referring to Table 1, the respiration rate step setting button 82b is divided by age and has a different respiration rate per minute 81a respectively according to each age group.

Referring to Table 2, as the flow rate increase step, a plurality of steps may be provided, and different times are set in minutes between the flow rate increase steps.

The respiration rate per minute 81a shows the sum of inhalation and exhalation made within one minute, and a flow rate increase step means the step at which the injection time rate proceeds to the next rate, and it is possible to set from the minute unit to hour unit.

An injection time rate shows the rate of time at which the nebulizer 70 atomizes during inhalation. For example, when the user selects Adult by the respiration rate step setting button 82b and sets 1 minute for the time of the flow rate increase step, the times of inhalation becomes 5 if the respiration rate per minute 81a is 10 times.

Therefore, the time of one inhalation becomes 6 seconds. At this time, the flow rate increase step begins at step 1, and it takes 1 minute, which was set, to proceed from step 1 to step 2. The injection time rate at step 1 is 1, and if the injection time rate is 1, the nebulizer 70 atomizes for 6 seconds of inhalation time.

As 1 minute has passed and proceeds to step 2, the injection time rate is changed to 1.1, so that the nebulizer 70 atomizes for 6.6 seconds of inhalation time. When another 1 minute has passed and proceeds to step 3, the injection time rate is changed to 1.2, so that the time of inhalation, that is, the injection time of air increases to 7.2 seconds.

Thus, the injection time of air increases step by step at the injection time rate depending on the injection time rate, and the user is subjected to the injection time of air that is increased by using the suction device 10 for hours or days so as to increase the time of inhalation naturally.

The function of inducing the inhalation time to increase may be applied to various types of suction devices in addition to the suction device 10.

Further, without limitation to the suction device 10, the technical configuration of the present invention may be applied to products for increasing vital lung capacity, and may be used as well by lung cancer patients, athletes, rhinitis patients, users who want to improve hypogastric breathing or abdominal breathing, melancholiacs and psychiatric patients.

For lung cancer patients, it is possible to partially improve the pulmonary function in which normal breathing is possible, and facilitate blood circulation to help with the treatment of lung cancer.

According to the present invention, athletes may train his or her pulmonary function by daytime exercise and also through the function of inducing the suction device 10 to increase the inhalation time even during sleep.

There is an effect of self-treatment for rhinitis patients by cultivating immunity through the function of inducing the increase of inhalation time and facilitating the blood circulation of the whole body and nose.

For the users who train hypogastric breathing or abdominal breathing, the effects are increased by improving pulmonary function and inducing abdominal breathing even during sleep through the function of inducing the increase of inhalation time.

Also, for students and office workers who need improved concentration, there are good effects that pulmonary function is improved and blood circulation is facilitated by the function of increasing the inhalation time so as to be helpful for not only concentration on study but also their health.

For psychiatric patients, stabilized breathing may improve the blood circulation of the brain and improve their physical condition. Therefore, physical stability induces mental stability, so that there is an effect of reducing the anxiety or depression of psychiatric patients.

Meanwhile, in one embodiment of the present invention, independently of the operation according to the values detected by the sensor unit 50 (a so-called automatic operation mode), it may also be set in such a manner that the movement into the bronchus of the tube unit according to a predetermined time cycle (for example, 1 hour) as set by an administrator such as a doctor through the input unit 80 in FIG. 8, and the foreign material sucking process through the suction pressure increase of the tube unit may be concurrently and repeatedly executed (a so-called semi-automatic operation mode).

According to the above-described configuration, even when a detection error has occurred in the sensor unit 50, automatic suction of foreign material according to a predetermined time cycle is executed, so that the patient may be prevented from encountering a dangerous situation.

Figure 10:
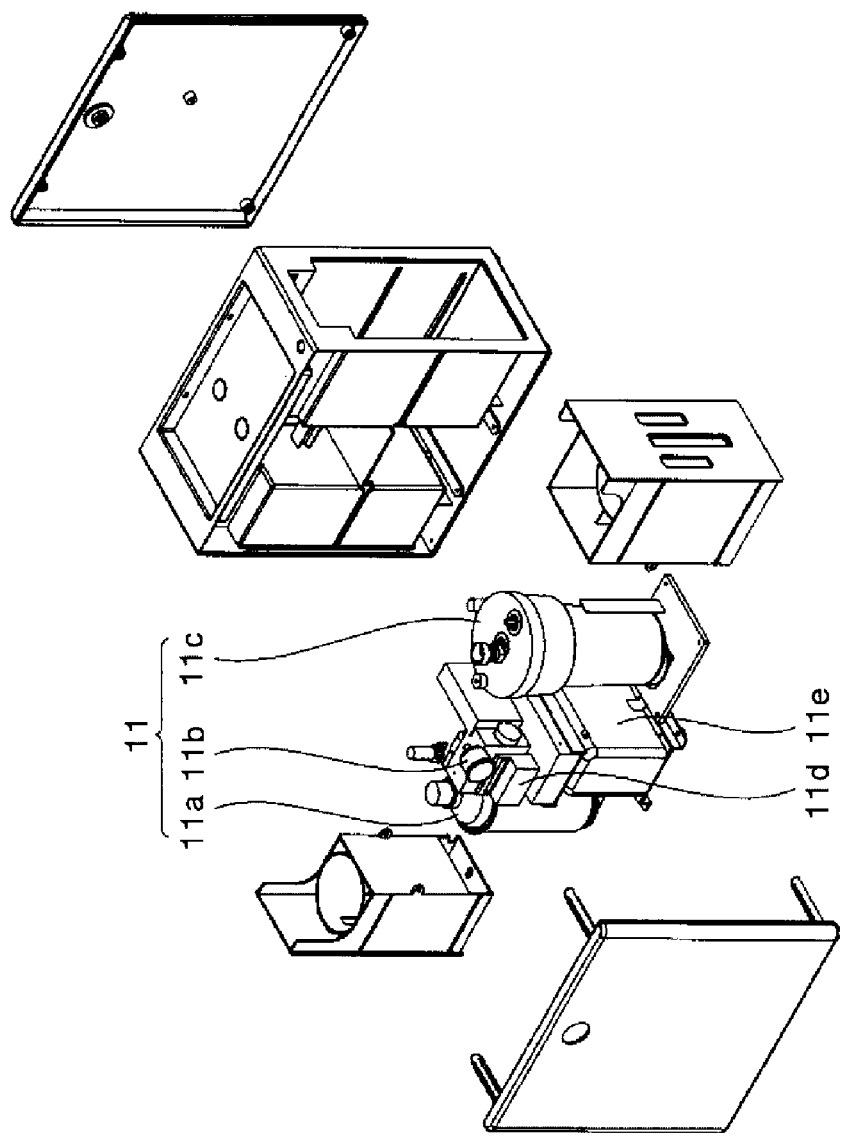
FIG. 10 is an exploded perspective view showing a second storage unit formed in a lower part of the suction device according to one embodiment of the present invention in FIG. 1.

FIG. 10 is an exploded perspective view showing a second storage unit 11 formed in the lower part of the suction device 10 of FIG. 1.

Referring to FIG. 10, the second storage unit 11 includes a suction container 11a, a thermal printer 11b, a saline water container 11c, a power supply 11d, and a motor 11e.

Referring to FIG. 1 and FIG. 10, the suction container 11a is filled with waste if the suction container 40b of FIG. 1 has no space to fill waste in. The saline water container 11c is also used as a storage container for filling saline water again in the saline water container 40a, when all of the saline water of the saline water container 40a of FIG. 1 has been used.

Therefore, the suction container 11a and the saline water container 11c have an advantage that they may be used if there are many users and it is difficult to manage from time to time.

The thermal printer 11b may be provided between the suction container 11a and the saline water container 11c to print a service record, patient's breathing condition, operation time, and breathing information within a predetermined period in which the suction device 10 was used.

Therefore, it is possible to confirm the present condition of the patient using the device by analyzing the information printed out and adequately treat the patient.

The power supply 11d is disposed below the thermal printer 11b to supply power to the motor 11e. The motor 11e is provided below the power supply 11d, and the motor 11e is driven for pumping to move waste to the suction container 11a or move the saline water in the saline water container 11c to the saline water container 40a.

For the suction device 10 whose frequency of use is high and which is used in hospital or at home, it is preferable to additionally provide the second storage unit 11 as described above.

Figure 11:
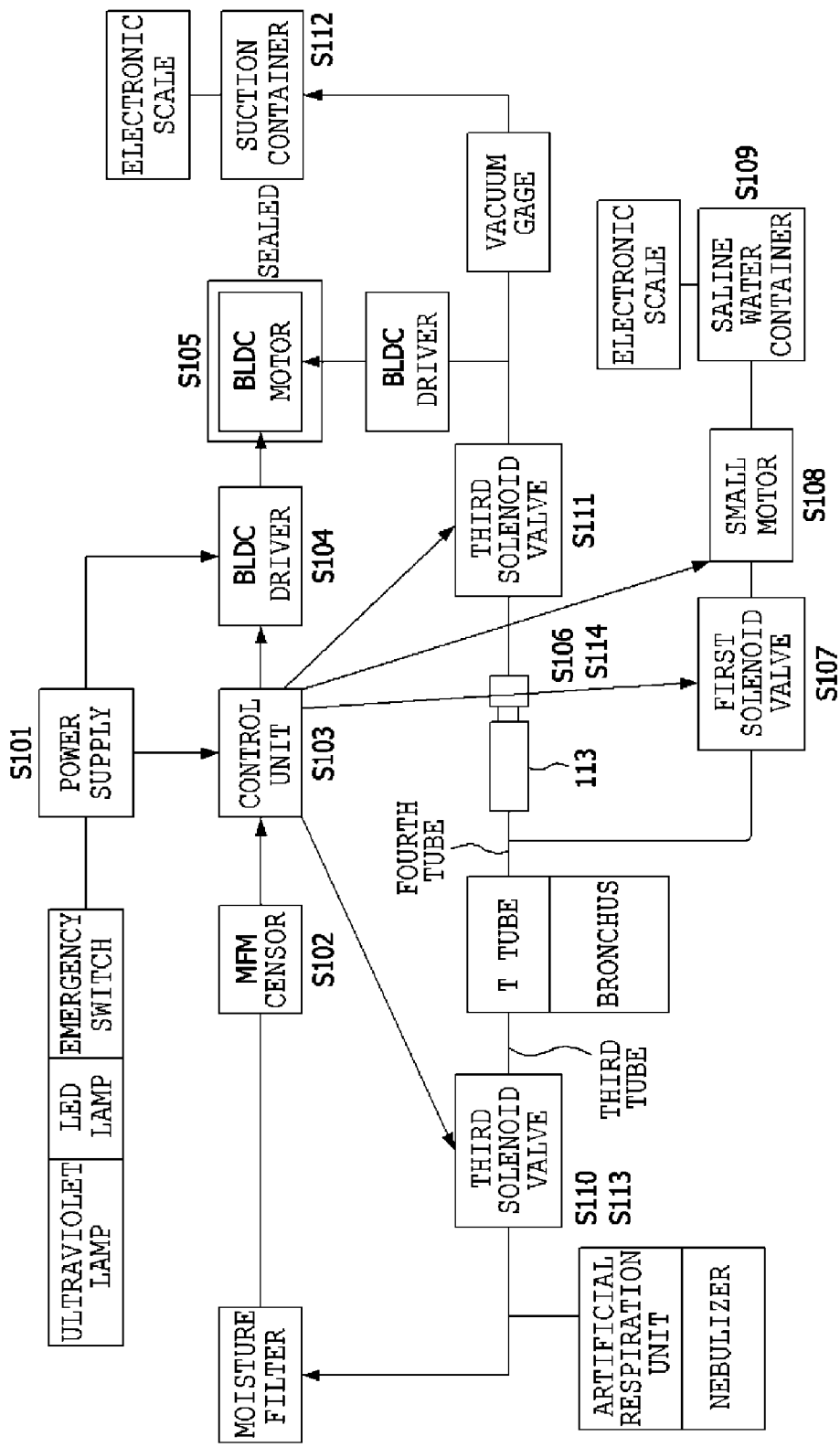
FIG. 11 is a block diagram showing a method of operating the suction device according to the present invention.

FIG. 11 is a block diagram showing a method of operating the suction device of FIG. 1.

The power supply 11d supplies power to the control unit 120 and the driver 30a (S101), and the MFM sensor 50a transmits to the control unit 120 the measured values for information on the mass of user's exhaled gas or daily breathing condition such as flow rate (S102).

Meanwhile, the control unit 120 analyzes the values measured by the MFM sensor 50a. If it is determined that foreign material is generated out of the daily breathing condition, the control unit 120 transmits a drive signal to the driver 30a (S103).

The driver 30a receives the drive signal from the control unit 120, and sends it to the BLDC motor 30b (S104). The BLDC motor 30b is driven by the signal received from the driver 30a, and at this time, outside air is supplied to the BLDC motor 30b through a moisture filter (S105).

Meanwhile, the catheter 113a moves through the catheter reel 113 to be inserted into the user's bronchus through the T tube 151 at a low speed, and is placed in the user's bronchus (S106). Herein, in order to increase the fluidity of foreign material before sucking it in through the catheter reel 113, the first solenoid valve 30c connected to the saline water container 40a is opened (S107).

Meanwhile, a small motor connected to the saline water container 40a is driven to suck saline water in the saline water container 40a (S108), and the saline water in the saline water container 40a passes through the first solenoid valve 30c and flows to the user's bronchus through the fourth tube 151f to increase the fluidity of the foreign materials.

Meanwhile, if it is determined that the weight of the saline water in the saline water container 40a is less than a predetermined reference value, the scale 100 provided below the saline water container 40a transmits the underweight signal representing the underweight of the saline water to the control unit 120 (S109).

When the first solenoid valve 30c is closed, the third solenoid valve 30c connected to the third tube 151e is also closed (S110), thereby the fluidity of foreign material is increased, and then the second solenoid valve 30c connected to the BLDC motor 30b through the fourth tube 151f is opened (S111).

Then, the second solenoid valve 30c is opened, so that foreign materials pass through the fourth tube 151f and the second solenoid valve 30c to be sucked at a predetermined pressure.

Meanwhile, the scale 100 provided below the suction container 11a measures the weight of foreign material. If it is determined that the weight of the foreign material exceeds the predetermined reference value, the scale 100 transmits the overweight signal representing the overweight of the foreign material to the control unit 120 (S112).

When foreign materials are sucked at a predetermined pressure, the second solenoid valve 30c is closed, and the third solenoid valve 30c is opened, and thereby the patient maintains the breathing condition. Meanwhile, the MFM sensor 50*a* measures the daily breathing condition of the user at all times (S113).

When foreign material is sucked through the catheter 113*a* and completely flows into the suction container 11*a*, the catheter reel 113 is driven to pull the catheter 113*a*. When the catheter 113*a* is discharged from the bronchus of the user, the inside and outside of the catheter 113*a* are cleaned by saline water (S114).

Meanwhile, since the BLDC motor 30*b* used in the present invention can, unlike the conventional AC motor, have the pressure, flow rate (NL/m) and the drive cycle of motor desired by the user changed easily through an increase and decrease of electric current, in the suction device 10, air injection is possible only for a user's inhalation without continuing air injection during a user's exhalation.

Further, since the BLDC motor 30*b* used in the present invention has excellent heat resistance with less noise, and does not generate an arc when it is turned on/off, its motor life is three times longer than the conventional AC motor, and may be made smaller with comparable performance, thereby it is suitable for use in a portable suction device and is stable.

Meanwhile, if the user has an inhalation time increased by using the suction device according to the present invention for several days, the user naturally comes to have a habit of abdominal respiration or a habit of long inhalation or exhalation. Thus, as the time of inhalation is increased, the user can gain the effects of blood circulation improvement and vital lung capacity improvement.

In addition, the present invention can induce natural respiration also for patients or infants whose pulmonary function is not good due to the aftereffects following surgery.

Further, since the catheter reel 113 of the present invention does not reside in the bronchus, it has an advantage that the inconvenience that the catheter 113*a* should be installed in the bronchus constantly is greatly reduced.

The suction device according to the present invention in which automatic suction and catheter insertion are possible may be used in most hospitals and homes for patients who need a guardian's help, thereby having industrial applicability.

While the present invention has been described with reference to the preferred embodiments, it will be understood by those skilled in the related art that various modifications and variations may be made therein without departing from the scope of the present invention as defined by the appended claims.

What is claimed is:

1. A suction device comprising:
   a drive unit configured to periodically pump;
   an input unit configured to input setting values for control;
   a sensor unit configured to measure a breathing condition of a patient;
   a tube unit configured to be inserted into a bronchus of a patient to suck foreign material generated in the bronchus, wherein the tube unit has a length that permits movement within the bronchus;
   wherein the tube unit comprises
      a first cuff configured to be positioned in the bronchus, to be inflated to expand the bronchus, and to be deflated;
      a second cuff configured to be positioned adjacent to and below the first cuff in the bronchus, to be inflated to expand the bronchus, and to be deflated;
      wherein the first cuff and second cuff are each alternately inflated and deflated at a predetermined interval of time in the bronchus such that the first cuff is inflated when the second cuff is deflated and such that the first cuff is deflated when the second cuff is inflated; and
   a control unit configured to receive the setting values and the measured results respectively transmitted from the input unit and the sensor unit and control the drive unit based on the received setting values and measured results.

2. The suction device of claim 1, wherein the drive unit includes a brushless DC motor (BLDC motor) that sucks and injects air by periodical pumping, and
   a driver that is connected to the BLDC motor at a distance and receives a control signal transmitted from the control unit to control the BLDC motor.

3. The suction device of claim 1, wherein the input unit includes:
   a breathing information display window in which a user's respiration rate per minute, a single respiratory air volume showing a volume breathed by a user at one time and breathing information showing respiration rate per hour are displayed; and
   a device setting window in which setting buttons for operating a respiratory function and suction are provided.

4. The suction device of claim 1, wherein the sensor unit includes:
   a mass flow meter (MFM sensor) configured to detect a daily breathing condition showing a patient's breathing pattern and a volume of exhaled gas for a predetermined time, transmit the detected results to the control unit, measure a mass of a patient's exhaled gas and the daily breathing condition to obtain measured results, and transmit the measured results of the daily breathing condition to the control unit.

5. The suction device of claim 4, wherein the control unit is configured to analyze the daily breathing condition received from the MFM sensor, and if it is determined that foreign material is generated in the body of the patient, control the drive unit to suck the foreign material, and
   analyze the daily breathing condition received from the MFM sensor, and if it is determined that the user's breathing condition is irregular and difficult, control the drive unit to assist with the user's respiratory function.

6. The suction device of claim 4, wherein the tube unit includes:
   a catheter reel and a tube cover,
      wherein the catheter reel comprises:
         a catheter that has a tube structure configured to be inserted into the bronchus to suck foreign material generated in the bronchus, wherein the catheter has a length that permits movement within the bronchus;
         a screw frame that includes a plurality of protruded threads formed on an outer circumference thereof on which the catheter is reeled, and is configured to push or pull the catheter, within the bronchus, depending on the rotation direction thereof;
         a catheter reel case that includes a plurality of holes to receive saline water for cleaning the catheter surface, and wherein the catheter reel case houses the catheter and the screw frame; and
         a stepping motor configured to rotate the screw frame to move the catheter within the bronchus, wherein the tube cover is outside of the catheter so that the catheter provides passages that are connected to a filter, the MFM sensor, a saline water container, and a nebulizer between the bronchus and catheter reel.

7. The suction device of claim 2, further comprising: a motor cover that encloses the BLDC motor to prevent a noise of the BLDC motor from being leaked to outside of the suction device and reduce a vibration of the BLDC motor.

8. The suction device of claim 1, wherein the tube unit further includes: a T tube,
wherein the T tube includes:
the first cuff;
the second cuff;
a first tube;
a second tube;
a third tube; and
a fourth tube;
wherein the third tube is connected to the first cuff to enable air to flow into and out of the first cuff to inflate and deflate the first cuff;
wherein the second tube is connected to the second cuff to enable air to flow into and out of the second cuff to inflate and deflate the second cuff;
wherein the first tube sucks foreign material formed above the first cuff when the first cuff is inflated; and
wherein the fourth tube sucks foreign material formed above the second cuff when the first cuff is deflated and the second cuff is inflated.

9. The suction device of claim 1, further comprising a storage unit which sucks and stores foreign material and stores and supplies saline water.

10. The suction device of claim 1, further comprising: a filter that prevents moisture from penetrating into the sensor unit, and waste from entering into the drive unit.

11. The suction device of claim 1, wherein the control unit is configured to analyze the daily breathing condition received from the MFM sensor, and if it is determined that foreign material is generated in the body of the patient, control the drive unit to suck the foreign material, and
analyze the daily breathing condition received from the MFM sensor, and if it is determined that the user's breathing condition is irregular and difficult, control the drive unit to assist with the user's respiratory function.

12. A suction device comprising:
a drive unit configured to periodically pump;
an input unit configured to input setting values for control;
a sensor unit configured to measure a breathing condition of a patient;
a control unit configured to receive the setting values and the measured results respectively transmitted from the input unit and the sensor unit and control the drive unit based on the received setting values and measured results;
a tube unit comprising a T tube,
wherein the T tube comprises
a first cuff configured to be positioned in the bronchus, to be inflated to expand the bronchus, and to be deflated;
a second cuff configured to be positioned adjacent to and below the first cuff in the bronchus, to be inflated to expand the bronchus, and to be deflated;
wherein when the first cuff and second cuff are each alternately inflated and deflated at a predetermined interval of time in the bronchus such that the first cuff is inflated when the second cuff is deflated and such that the first cuff is deflated when the second cuff is inflated;
a first tube;
a second tube;
a third tube; and
a fourth tube;
wherein the third tube is connected to the first cuff to inflate and deflate the first cuff;
wherein the second tube is connected to the second cuff to inflate and deflate the second cuff;
wherein the first tube sucks foreign material formed above the first cuff, when the first cuff is inflated, to move the foreign material out of the bronchus; and
wherein the fourth tube sucks foreign material formed above the second cuff, when the first cuff is deflated and the second cuff is inflated, to move the foreign material out of the bronchus.

13. The suction device of claim 12, wherein the drive unit includes a brushless DC motor (BLDC motor) that sucks and injects air by periodical pumping, and
a driver that is connected to the BLDC motor at a distance and receives a control signal transmitted from the control unit to control the BLDC motor.

14. The suction device of claim 12, wherein the input unit includes:
a breathing information display window in which a user's respiration rate per minute, a single respiratory air volume showing a volume breathed by a user at one time and breathing information showing respiration rate per hour are displayed; and
a device setting window in which setting buttons for operating a respiratory function and suction are provided.

15. The suction device of claim 12, wherein the sensor unit includes:
a mass flow meter (MFM sensor) that is configured to detect a daily breathing condition showing a patient's breathing pattern and a volume of exhaled gas for a predetermined time, transmit the detected results to the control unit, measure a mass of a patient's exhaled gas and the daily breathing condition to obtain measured results, and transmit the measured results of the daily breathing condition to the control unit.

16. A suction device comprising:
a drive unit configured to periodically pump;
an input unit configured to input setting values for control;
a sensor unit configured to measure a breathing condition of a patient;
a control unit configured to receive the setting values and the measured results respectively transmitted from the input unit and the sensor unit and control the drive unit based on the received setting values and measured results;
a tube unit comprising a catheter reel and a tube cover,
wherein the catheter reel comprises:
a catheter that has a tube structure configured to be inserted into a bronchus of a patient to suck foreign material generated in the bronchus, wherein the catheter has a length that permits movement within the bronchus;
a screw frame configured to push or pull the catheter, within the bronchus, depending on the rotation direction thereof;
a catheter reel case that includes a plurality of holes to receive saline water for cleaning the catheter surface, and wherein the catheter reel case houses the catheter and the screw frame; and a stepping motor configured to rotate the screw frame to move the catheter within the bronchus;
wherein the tube cover is outside of the catheter so that the catheter provides passages that are connected to a saline water container and a nebulizer between the bronchus and the catheter reel.

17. The suction device of claim 16, wherein the tube unit further comprises
a first cuff configured to be positioned in the bronchus, to be inflated to expand the bronchus, and to be deflated;
a second cuff configured to be positioned adjacent to and below the first cuff in the bronchus, to be inflated to expand the bronchus, and to be deflated;
wherein when the first cuff and second cuff are each alternately inflated and deflated at a predetermined interval of time in the bronchus such that the first cuff is inflated when the second cuff is deflated and such that the first cuff is deflated when the second cuff is inflated.

18. The suction device of claim 17, wherein the tube unit comprises a T tube,
wherein the T tube comprises
a first tube;
a second tube;
a third tube; and
a fourth tube;
wherein the third tube is connected to the first cuff to inflate and deflate the first cuff;
wherein the second tube is connected to the second cuff to inflate and deflate the second cuff;
wherein the first tube sucks foreign material formed above the first cuff, when the first cuff is inflated, to move the foreign material out of the bronchus; and
wherein the fourth tube sucks foreign material formed above the second cuff, when the first cuff is deflated and the second cuff is inflated, to move the foreign material out of the bronchus.

19. The suction device of claim 16, further comprising
a storage unit that sucks and stores foreign material and stores and supplies saline water.

20. The suction device of claim 16, wherein the drive unit includes a brushless DC motor (BLDC motor) that sucks and injects air by periodical pumping, and
a driver that is connected to the BLDC motor at a distance and receives a control signal transmitted from the control unit to control the BLDC motor.

21. The suction device of claim 16, wherein the input unit includes:
a breathing information display window in which a user's respiration rate per minute, a single respiratory air volume showing a volume breathed by a user at one time and breathing information showing respiration rate per hour are displayed; and
a device setting window in which setting buttons for operating a respiratory function and suction are provided.

22. The suction device of claim 16, wherein the sensor unit includes:
a mass flow meter (MFM sensor) that is configured to detect a daily breathing condition showing a patient's breathing pattern and a volume of exhaled gas for a predetermined time, transmit the detected results to the control unit, measure a mass of a patient's exhaled gas and the daily breathing condition to obtain measured results, and transmit the measured results of the daily breathing condition to the control unit.

23. The suction device of claim 22, wherein the control unit is configured to analyze the daily breathing condition received from the MFM sensor, and if it is determined that foreign material is generated in the body of the patient, control the drive unit to suck the foreign material, and
analyze the daily breathing condition received from the MFM sensor, and if it is determined that the user's breathing condition is irregular and difficult, control the drive unit to assist with the user's respiratory function.

* * * * *